US012685444B2

(12) United States Patent
Batchelor et al.

(10) Patent No.: US 12,685,444 B2
(45) Date of Patent: Jul. 21, 2026

(54) ANALYSIS OF REFLECTED SIGNALS DURING A LASER PROCEDURE

(71) Applicant: GYRUS ACMI, INC., Westborough, MA (US)

(72) Inventors: Kester Julian Batchelor, Mound, MN (US); Sergey A. Bukesov, Acton, MA (US); Kurt G. Shelton, Bedford, MA (US); Charles A. Baker, Rogers, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 136 days.

(21) Appl. No.: 18/590,596

(22) Filed: Feb. 28, 2024

(65) Prior Publication Data

US 2024/0306920 A1     Sep. 19, 2024

Related U.S. Application Data

(60) Provisional application No. 63/490,686, filed on Mar. 16, 2023.

(51) Int. Cl.
*A61B 5/00*          (2006.01)
*A61B 1/06*          (2006.01)
*G16H 50/20*        (2018.01)

(52) U.S. Cl.
CPC .......... *A61B 5/0075* (2013.01); *A61B 1/0676* (2013.01); *A61B 5/0077* (2013.01); *G16H 50/20* (2018.01); *A61B 2562/02* (2013.01)

(58) Field of Classification Search
CPC ... A61B 5/0075; A61B 1/0676; A61B 5/0077; A61B 2562/02; A61B 1/063;

(Continued)

(56) References Cited

U.S. PATENT DOCUMENTS 8,046,057 B2 * 10/2011 Clarke ............... A61B 17/3211
                                                                    600/478
12,471,992 B2 * 11/2025 Shelton ............... A61B 5/0075
                            (Continued)

FOREIGN PATENT DOCUMENTS

DE          102024106134 A1      9/2024
WO          WO-2016201092 A1 * 12/2016   ........... A61B 5/0084
WO          WO-2022032211 A1 *  2/2022   ............. A61B 18/22

OTHER PUBLICATIONS

"Japanese Application Serial No. , Notice of Reason for Refusal filed Oct. 28, 2025", W/ English Translation, 6 pages.

*Primary Examiner* — John R Schnurr
(74) *Attorney, Agent, or Firm* — Schwegman Lundberg & Woessner, P.A.

(57)          ABSTRACT

A system for analyzing a reflected signal during a laser procedure can include a surgical scope. A first light source emitter can be configurable to emit a first signal having a first (e.g., a non-visible) spectrum. A second light source emitter can be configurable to emit a second signal having a second spectrum (e.g., a visible or infrared (IR) spectrum). Each of the first or the second light source emitters can be coupled to or included within the surgical scope. The system can include an optical sensor configurable to detect and analyze a third signal returned from the surface of an object in response to the emitted second signal. The returned third signal can be analyzed to determine whether a reflected absolute or relative intensity or an absolute or relative spectral signature meets at least one criterion, thereby triggering at least one of: warning a user or adjusting the first signal.

19 Claims, 5 Drawing Sheets

(58) Field of Classification Search
CPC ....... A61B 1/0638; A61B 1/0655; A61B 1/07;
A61B 5/0084; A61B 18/26; A61B
2018/00898; A61B 2018/00982; G16H
50/20
See application file for complete search history.

(56) References Cited

U.S. PATENT DOCUMENTS

| | | | |
|---|---|---|---|
| 2007/0232887 A1* | 10/2007 | Bettesh .................. | A61B 1/041 |
| | | | 600/101 |
| 2009/0281536 A1* | 11/2009 | Beckman ............. | A61B 5/0059 |
| | | | 606/41 |
| 2013/0138018 A1* | 5/2013 | Gertner ................ | A61N 5/0601 |
| | | | 601/2 |
| 2014/0200406 A1* | 7/2014 | Bennett .................. | A61B 1/127 |
| | | | 600/109 |
| 2015/0230864 A1* | 8/2015 | Xuan ..................... | A61B 18/22 |
| | | | 606/2.5 |
| 2018/0114319 A1* | 4/2018 | Kono ..................... | A61B 1/018 |
| 2020/0197094 A1 | 6/2020 | Fan et al. | |
| 2021/0015507 A1* | 1/2021 | Roberts .................. | A61B 18/26 |
| 2021/0038300 A1* | 2/2021 | Bukesov ............ | A61B 1/00165 |
| 2021/0038304 A1* | 2/2021 | Bukesov ............... | A61B 18/26 |
| 2021/0038309 A1* | 2/2021 | Talbot .................. | A61B 5/0075 |
| 2022/0313062 A1* | 10/2022 | Polejaev ................... | G01J 3/28 |
| 2022/0361951 A1* | 11/2022 | Brinkmann ............ | A61B 18/26 |
| 2023/0033644 A1* | 2/2023 | Bukesov ............. | A61B 18/201 |
| 2023/0270496 A1* | 8/2023 | Shelton ................. | A61B 18/22 |
| 2023/0277244 A1* | 9/2023 | Granot .............. | G02B 23/2423 |
| | | | 600/310 |
| 2023/0285079 A1* | 9/2023 | Brinkmann ............ | A61B 18/20 |
| 2024/0016543 A1* | 1/2024 | Altshuler ............... | A61B 18/22 |
| 2024/0306920 A1* | 9/2024 | Batchelor ........... | A61B 1/0676 |

* cited by examiner

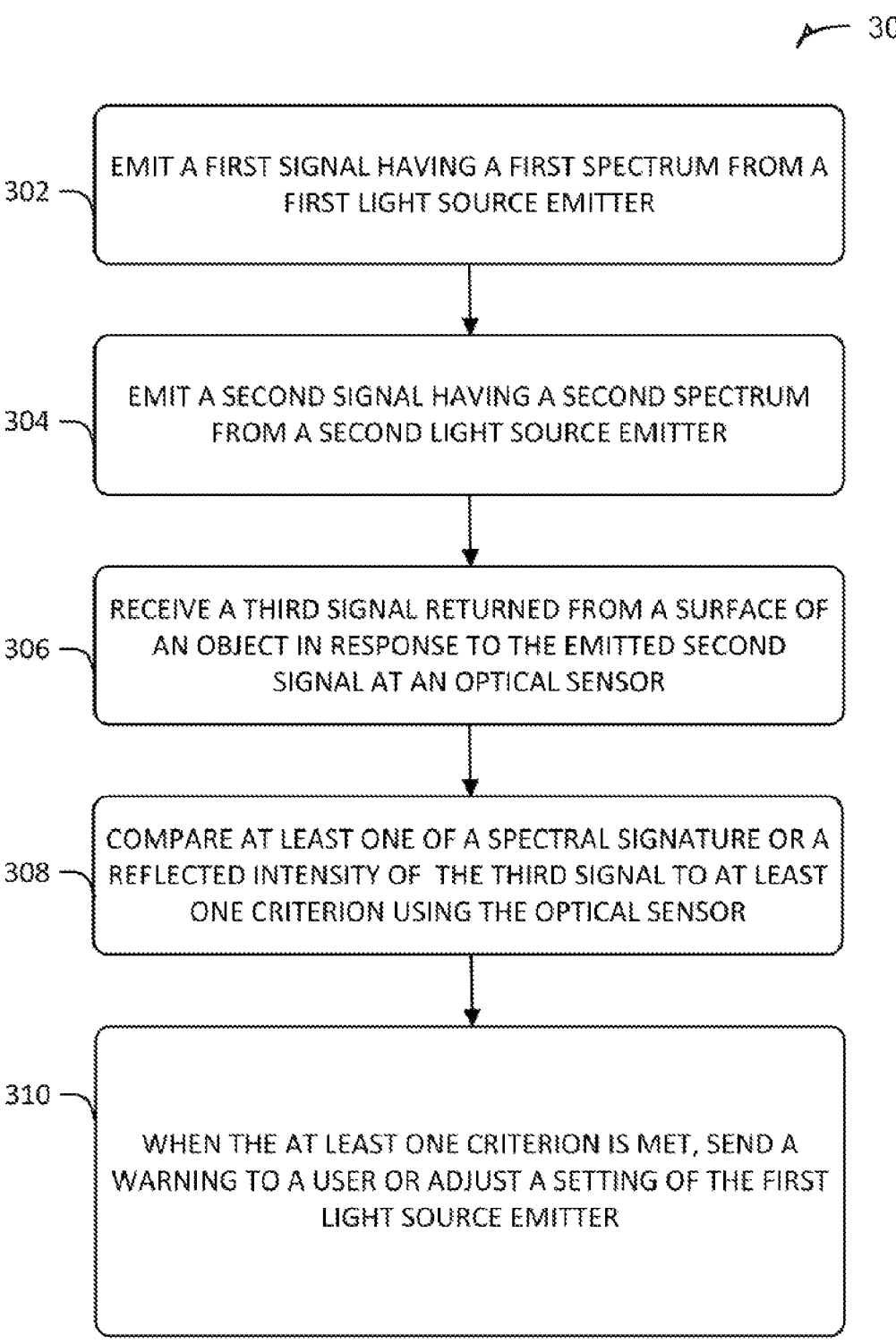

300

302 — EMIT A FIRST SIGNAL HAVING A FIRST SPECTRUM FROM A FIRST LIGHT SOURCE EMITTER

304 — EMIT A SECOND SIGNAL HAVING A SECOND SPECTRUM FROM A SECOND LIGHT SOURCE EMITTER

306 — RECEIVE A THIRD SIGNAL RETURNED FROM A SURFACE OF AN OBJECT IN RESPONSE TO THE EMITTED SECOND SIGNAL AT AN OPTICAL SENSOR

308 — COMPARE AT LEAST ONE OF A SPECTRAL SIGNATURE OR A REFLECTED INTENSITY OF THE THIRD SIGNAL TO AT LEAST ONE CRITERION USING THE OPTICAL SENSOR

310 — WHEN THE AT LEAST ONE CRITERION IS MET, SEND A WARNING TO A USER OR ADJUST A SETTING OF THE FIRST LIGHT SOURCE EMITTER

FIG. 3

ANALYSIS OF REFLECTED SIGNALS DURING A LASER PROCEDURE

PRIORITY CLAIM

This application claims the benefit of priority to U.S. Provisional Patent Application Ser. No. 63/490,686, filed Mar. 16, 2023, the contents of which are hereby incorporated by reference in their entirety.

TECHNICAL FIELD

The present disclosure relates to analysis of reflected signals during diagnostic or therapeutic laser procedures.

BACKGROUND

Laser procedures, such as laser lithotripsy, use laser systems that may employ both visible and non-visible light to illuminate and/or treat targets such as a tumor or a calculus ("stone"), or tissue in a patient's body. Use of laser energy during procedures may be limited by concerns about the possibility of stray laser energy affecting non-target tissue.

SUMMARY

Laser energy can be used during medical procedures. In laser lithotripsy procedures, a target, such as a kidney stone can be reduced or ablated to allow for fragments or dust from the stone to be naturally passed out of the body, or to allow stone fragments to be removed from the body such as via suction or a retrieval device. In other procedures, laser energy can be used to treat tissue, such as by cutting tissue, cauterizing a site, or the like. The targets, such as stone or target tissue to be cut, cauterized, or otherwise treated can be located close to, or surrounded by, healthy, non-target tissue that can be affected by stray laser energy.

Many surgical procedures can also employ other medical devices such as a guidewire made from material such as magnesium oxide (MgO), a fluoropolymer such as Teflon™, stainless steel, nickel-titanium, also referred to as nitinol, a polymer, plastic, or another similar shiny or highly light-reflective material (when compared to tissues such as Ureter tissue, Bladder tissue, or when compared to a stone). Similarly, devices such as a surgical stent or a surgical screw can be formed from highly reflective material and can be implanted into a portion of a patient's body. When a device or other object made from a highly reflective material is located in the same environment, region, or part of the body as a laser fiber, using the laser fiber can be raise the possibility of stray laser energy being reflected off a highly reflective surface and affecting healthy, non-target tissue.

The present inventors have recognized, among other things, that an optical sensor or optical transducer and analyzer coupled to a surgical scope, such as an in-vivo-insertable therapeutic or diagnostic endoscope including a laser fiber, can be used to detect and analyze a signal returned from the surface of an object. Specifically, the optical sensor can be configurable to detect and analyze an absolute or relative reflected intensity or an absolute or relative spectral signature of a signal (e.g., an absolute or relative value of the reflected intensity or the spectral signature), or any property of a spectra reflection returned from a surface of the object, such as explained further below. For example, when the reflected intensity of the signal returned from the surface of the object meets at least one criterion (e.g., falls below a lower-threshold value or exceeds an upper-threshold value), a controller coupled to the optical sensor can, in response, cause a warning or notification to be provided (e.g., on a user interface) or the controller can adjust laser emission (e.g., changing the intensity of the laser radiation or disabling the laser emitter). Similarly, a spectral signature returned from a surface of the object can constitute a number of spectral intensities at specific wavelengths of interest. When such a spectral signature meets a similarity criterion (e.g., to a spectral signature template of a known composition target in a library of such spectral signature templates) a controller coupled to the optical sensor can, in response, cause a warning or notification to be provided (e.g., on a user interface) or the controller can adjust laser emission (e.g., changing the intensity of the laser radiation or disabling the laser emitter).

A system for analyzing a reflected signal during a laser procedure can include a surgical scope, such as an endoscope. A first light source emitter can be coupled to or included within the surgical scope. The first light source emitter can include a laser diode or any emission source capable of emitting a first signal having a non-visible spectrum or wavelength capable of providing diagnostic or therapeutic radiation. The system can further include a second light source emitter coupled to or included within the surgical scope. In an example, the second light source emitter can include an endoscopic light source or any emission source capable of emitting a second signal having a visible spectrum or wavelength. In another example, the second light source emitter can be an infrared (IR) light source having an emission wavelength close to that of the laser light source. Thus, the system can include a laser emitter to emit non-visible radiation or light, such as from or through a laser fiber, at wavelengths capable of performing diagnostic or therapeutic laser procedures, a visible light source, such as light attached to the scope to emit visible light to illuminate a target, portions of anatomy, a surgical field, etc., and/or an IR light source.

The system can also include an optical sensor. The optical sensor can be included as a part of a machine or computer, a spectrometer, or the like, such as can be coupled to the scope. The optical sensor can be configurable to detect and analyze a third signal (e.g., a return signal) returned from a surface of an object in response to the emitted second or visible light signal. Controller circuitry coupled to the optical sensor can be configurable to warn a user and/or adjust the first signal or the laser signal when a reflected intensity of the third signal falls below a lower-threshold value or exceeds an upper-threshold value. In an example, a spectrometer can be included to perform spectral analysis on a return signal. When the reflected intensity of the return signal exceeds the upper-threshold value, the controller circuitry can cause the spectrometer to interrupt or terminate spectral analysis of the return signal.

In this disclosure, the terms first signal, non-visible light signal, laser signal, or laser radiation may be used interchangeably. Additionally, the terms second signal, endoscopic light signal and visible light signal may be used interchangeably, as may the terms third signal and return signal. Also, the terms first light source, aiming beam light source, first light source emitter, and laser emitter may be used interchangeably. Finally, the terms second light source emitter, visible light source, endoscopic light source, and visible light emitter may be used interchangeably. And, in some examples, the terms second light source emitter and IR light source emitter can be used interchangeably, with the IR light source replacing or being in addition to, a visible light source.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 3 illustrates an example diagram of a method for analysis of a reflected signal during an in-vivo-insertable medical procedure.

DETAILED DESCRIPTION

Figure 1:
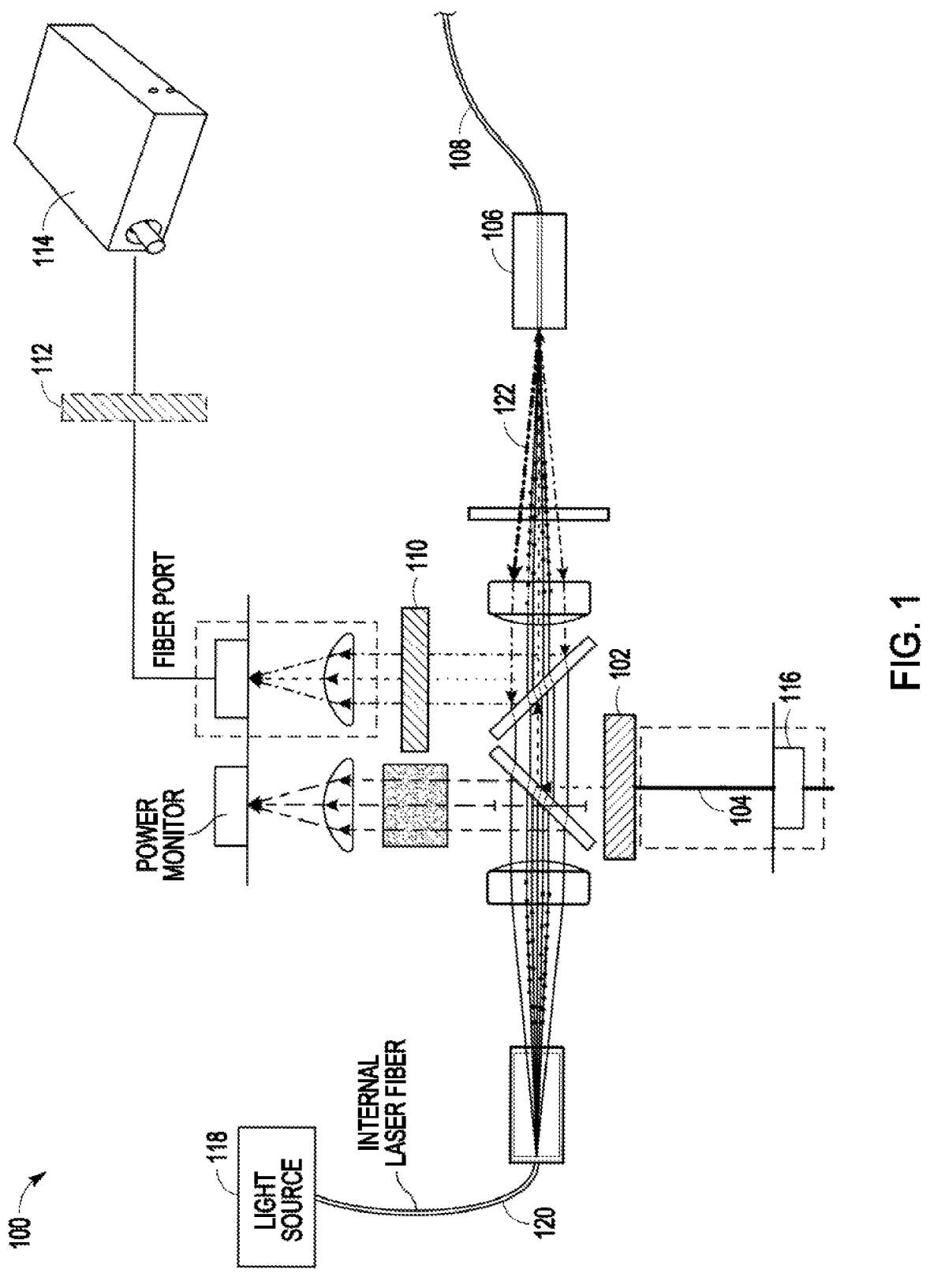
FIG. 1 illustrates an example of components within a laser system.

The present systems and methods can help in safely using laser energy or laser radiation by analyzing a reflected signal detected during a diagnostic or therapeutic laser procedure. Surgical laser procedures, such as laser lithotripsy, use laser energy to reduce or break up stones, cut, cauterize, or otherwise treat tissue, remove tumors, or the like. Laser energy can pose a potential issue to otherwise healthy tissue which can be near a target such as a stone, or can be next to or surround target tissue to be treated during the procedure. Specific types of lasers, such as green-light or blue-light lasers can be especially challenging as such lasers emit energy at a wavelength that is not absorbed by water and can thus cause unintended tissue effects if the energy contacts non-target tissue. In fact, green-light and blue-light lasers are usually included in a special (and very expensive) laser fiber known as a side-fire laser, which only allows the energy to be emitted at a 90-degree angle to better control where the laser energy is being aimed. Even non-green or non-blue light lasers can affect non-target tissue if stray energy makes contact with non-target tissue. In a procedure involving other medical devices such as a stone capture device (e.g., basket), guidewires, clamps, or the like, which can often be made from a highly reflective material such as surgical-grade stainless steel, a fluoropolymer such as Teflon™, MgO, or the like, stray laser radiation can deflect or bounce off the objects and impact surrounding, non-target, tissue.

A system for analyzing a reflected signal during a laser procedure can comprise a surgical scope, such as an endoscope, which can include a laser light emitter and a visible light emitter. The laser light emitter can be coupled to a laser fiber that couples to an endoscopic system; the laser light emitter can be configured to emit a first signal having a non-visible wavelength or spectrum (e.g., a wavelength in a range between 800 nanometers (nm) and 900 nm) for target diagnosis or treatment. The visible light emitter can be included on or attached to the endoscope and be configurable to emit a second signal having a visible light spectrum or wavelength (e.g., a wavelength in a range between 400 nm and 750 nm.) In some embodiments, an IR light source having an emission wavelength close to that of the laser light source can be optionally coupled to the endoscope. The visible light emitter and/or an (IR) light source can be located such as to be emitted through the laser fiber, for example near the laser light emitter. The visible light emitter and/or IR light source can be used to illuminate a target, a portion of anatomy, or a surgical field in which the medical procedure is to take place. The visible light source and/or the IR light source can be used to illuminate the target or object of interest; and reflections from the target or object in response thereto can be analyzed, spectroscopically or otherwise, such as to determine one or more target characteristics, such as target composition, target size, or the like.

An optical sensor coupled to at least one of the surgical fiber, the laser light emitter, the visible light emitter, or the endoscope can be configurable to detect a third signal returned from a surface of an object (e.g., a target, a medical device, an implanted object, etc.) in response to the emitted second or visible light signal. The third signal from the object can be a reflected signal, a scattered signal (e.g., via RAMAN scattering), fluorescence, or the like. A controller or controller circuitry, coupled to the optical sensor, can be configurable to analyze the third signal and, based on the analysis, cause a warning to be emitted or transmitted, so as to warn a user such as a physician when a reflected absolute or relative intensity of the third signal meets a criterion and/or when an analysis of an absolute or relative spectral signature of the third signal meets a criterion. For example, a warning can be triggered when the reflected intensity of the third signal falls below a lower-threshold value or exceeds an upper-threshold value. A reflected intensity below the lower-threshold value can correspond to the lack of an object reflecting the visible light and a reflected intensity above the upper-threshold value can correspond to light being reflected off of a highly-reflective surface or object (e.g., a stone retrieval device). In another example, a warning can be triggered when the spectral intensity or spectral signature analysis of the third signal reveals information about a composition of the target or information about a change in composition of the target. As mentioned, this can include computing a similarity score of the spectral signature of a target of interest in comparison to a spectral signature of one or more templates (e.g., corresponding to different compositions) that can be stored in a library for later comparison.

In an example, the warning can be visual, such as displayed on a graphical user interface (GUI) or monitor connected to the system, illuminating a light emitting diode (LED) or button on the endoscope (e.g., a button or LED on a handpiece), causing the visible light signal to flash or change color, or some combination thereof. In another example, the warning can be haptic, such as causing the handpiece of the endoscope to vibrate, or the warning can be audible, such as emitting a sound through a speaker on the handpiece, through the GUI, etc. Additionally, or alternative, the warning can be sent as one or more visual, one or more haptic, and/or one or more audible warnings, as desired.

A warning to the physician provides the physician with an option to adjust the laser intensity, turn off the laser emission, accept a changed setting for the laser emission, or the like. Alternatively, in some examples, the controller circuitry can cause automatic adjustment of the laser emitter based on the reflected intensity. For example, the controller circuitry can cause a change to the intensity of the laser emission, disable or lock the laser emitter, or otherwise inhibit or prevent laser emission until the reflected intensity falls between the lower-threshold value and the upper-threshold value.

Such a system can result in safer medical procedures by reducing or preventing unintended tissue effects, which can result in better and/or faster patient recovery. Additionally, by warning a physician or locking laser emission when no target or object is detected, blue light and green light lasers can be used in non-side-fire laser fibers as the laser radiation will not be emitted unless a proper or intended target is reflecting the visible light, thereby reducing the cost of the laser fibers. Furthermore, using a fully automatic system in which an Artificial Intelligence (AI) or Machine Learning (ML) driven system controls the laser output can result in more efficient medical procedures as the system can react faster than a human user.

FIG. 1 illustrates an example of components within a laser system 100. The laser system 100 can be coupled to an endoscopic system, such as an in-vivo insertable therapeutic or diagnostic endoscopic system, for performing patient diagnosis or treatment. Description of examples regarding how the laser system 100 can be connected to an endoscopic system can be found in U.S. patent application Ser. No. 16/984,447, the contents of which are incorporated in their entirety. In the example illustrated in FIG. 1, the laser system 100 can include a light source 118 (e.g., a laser module or component), which can emit a signal such as laser radiation to ablate tissue, break up a stone (e.g., a kidney stone or a gallstone) or perform any suitable therapeutic or diagnostic procedure, and can emit signals in the visible spectrum or the non-visible spectrum. The light source 118 can be connected to and emit the laser radiation through a laser fiber 120, which can in turn be connected to, an optical coupler or other housing within which various optical components (such as those discussed below) can be included.

Optionally, an aiming beam 104 emitted from an aiming beam emission source 116 can denote, mark, or the like, the location of where the light from the light source 118 is aimed (or to be aimed), emitted, transmitted, etc., (e.g., when the light or radiation from the aiming beam is emitted in a visible spectrum). A first optical component 102 (e.g., a filter) can be located at an output of the aiming beam emission source 116 and can be at least equal to or slightly larger than the diameter of the aiming beam 104. The first optical component 102 can remove the sources of noise (e.g., the spectrum spread of the main frequency/wavelength of the aiming beam 104), which can significantly improve the signals detected from the target or object 106.

Thus, in the example of FIG. 1, a signal emitted from the aiming beam emission source 116 can be filtered, attenuated, blocked, polarized, or otherwise affected by the first optical component 102, so that only signals of desired wavelengths and intensities are emitted from the surgical fiber 108 and reach the object 106. In an example, at least a portion of a signal emitted from the surgical fiber 108 can be reflected back from the object 106 (as denoted by the arrows). The laser system 100 can additionally include one or more additional optical components (e.g., second optical component(s)), such as one or more notch filters 110 and 112 (or any suitable filter(s)) located in an optical path between the object 106 and a spectrometer and/or an analyzer located in the feedback componentry 114. The notch filters 110 and 112 can be used to remove any reflection signals reflected back from the object 106 with frequencies or wavelengths around, near, or substantially close to those of the aiming beam 104.

In an example, the object 106 can be a calculus or stone to be treated during a medical procedure. In some cases, the object 106 can be a medical device or an implanted device within a patient, a portion of non-targeted tissue, or the like. At least a portion of the light from the aiming beam 104 and/or an endoscopic light source such as one or more light-emitting diodes or xenon light source (not shown) can be reflected off of the object 106. Such a reflected light signal 122 can travel back toward and into the surgical fiber 108 and the laser fiber 120 where it can be deflected, refracted, dispersed, or otherwise directed or adjusted by one or more optical components (e.g., lenses, filters, etc.) and ultimately directed to the feedback componentry 114 which can include or be connected to one or more of an optical transducer, an optical detector, spectrometer, analyzer, or other circuitry or components capable of detecting and/or analyzing the reflected light signal 122. The feedback componentry 114 can be included in or connected to a machine or computer such as that discussed with respect to FIG. 4 below.

The reflected light signal 122 from the object 106 can be analyzed to determine a spectral signature of the reflected light signal 122. For example, the spectral signature can include a reflected intensity at each of different specific light or signal wavelengths in the spectrum; alternatively, the spectral signature can include a ratio of wavelength intensities at different wavelengths, a shape of the spectral signal in the spectrum, or the like. In an example, controller circuitry coupled to the feedback componentry 114 can use the absolute or relative value of the peak intensity of the reflected light signal 122 to determine whether the value of the reflected intensity meets a criterion such as being below a lower-threshold value or above an upper-threshold value. In response to one or both of these determinations, the controller circuitry can provide a notification to the physician, such as a warning, or can adjust an intensity of a laser signal, disable or lock the laser emitter, recommend new laser settings to the physician, or a combination thereof.

In such an example, the reflected intensity of the reflected light signal 122 exceeding the upper-threshold value can correspond to the object 106 being highly reflective, such as being comprised of a material such as magnesium oxide (MgO), metal, stainless steel, nitinol, a fluoropolymer such as Teflon™, a polymer, a plastic, or a combination thereof. In an example when the object 106 is a medical device (e.g., a basket), the system can warn the physician to or recommend that the physician stop laser emission or not begin laser emission. Additionally, or alternatively, in such an example the system can disable, terminate, or prevent laser emission, such as until the laser fiber 120 and/or the surgical fiber 108 is pointed away from the object 106, such as may be indicated by a corresponding drop in intensity of reflected light. On the other hand, in certain medical procedures, such as the removal of a surgical mesh, if it is determined that the object 106 should be cut, the system can adjust the intensity of the laser emission or can recommend to the user a particular intensity value or range of the laser emission to use the laser to cut the object 106 while reducing or minimizing the risk of causing damage to surrounding tissue.

A reflected intensity of the reflected light signal 122 falling below the lower-threshold value (or the absence of a reflected signal) can correspond to no target or object being detected, such as when the light signal from the aiming beam 104 and/or an endoscopic light source (not shown) is being reflected by water or tissue having a low reflected intensity. In such a case, one or more laser emission sources (e.g., a green-light laser emitter or a blue-light laser emitter, or the emitter of any laser emitting a signal having a wavelength that is not absorbed or poorly absorbed by water) 118 can be locked, disabled, shut-off, or the like, by the system until the laser fiber 120 and/or the surgical fiber 108 can be repositioned. Thus, in an example, the system can be set to operate in a partially automatic manner in that it can monitor the reflected intensity of a return signal, and warn, notify, etc., a physician or other user of the system of the presence of a highly reflective object (e.g., basket) or low reflective object (e.g., water) in the path of the laser light. Optionally, the system can additionally or alternatively recommend a course of action to the physician. Alternatively, the system can be set to operate in a fully automatic manner such that when a reflected intensity is above the upper-threshold value or below the lower-threshold value the system can respond appropriately. This response of the system can be to reduce the intensity or power of a laser emission, to lock, disable, or prevent a laser emission, to cause the endoscope, the laser fiber and/or the surgical fiber to be repositioned, or take any other suitable corrective action. The laser system 100 can be included in the endoscopic system and can comprise one or more laser emitters (e.g., laser diodes), one or more aiming beam light sources, and/or one or more visible light emitters. Thus, a signal from a laser or non-visible light emitter and/or a visible light emitter can be transmitted through the laser fiber 120 and the surgical fiber 108 toward the object 106.

Figure 2:
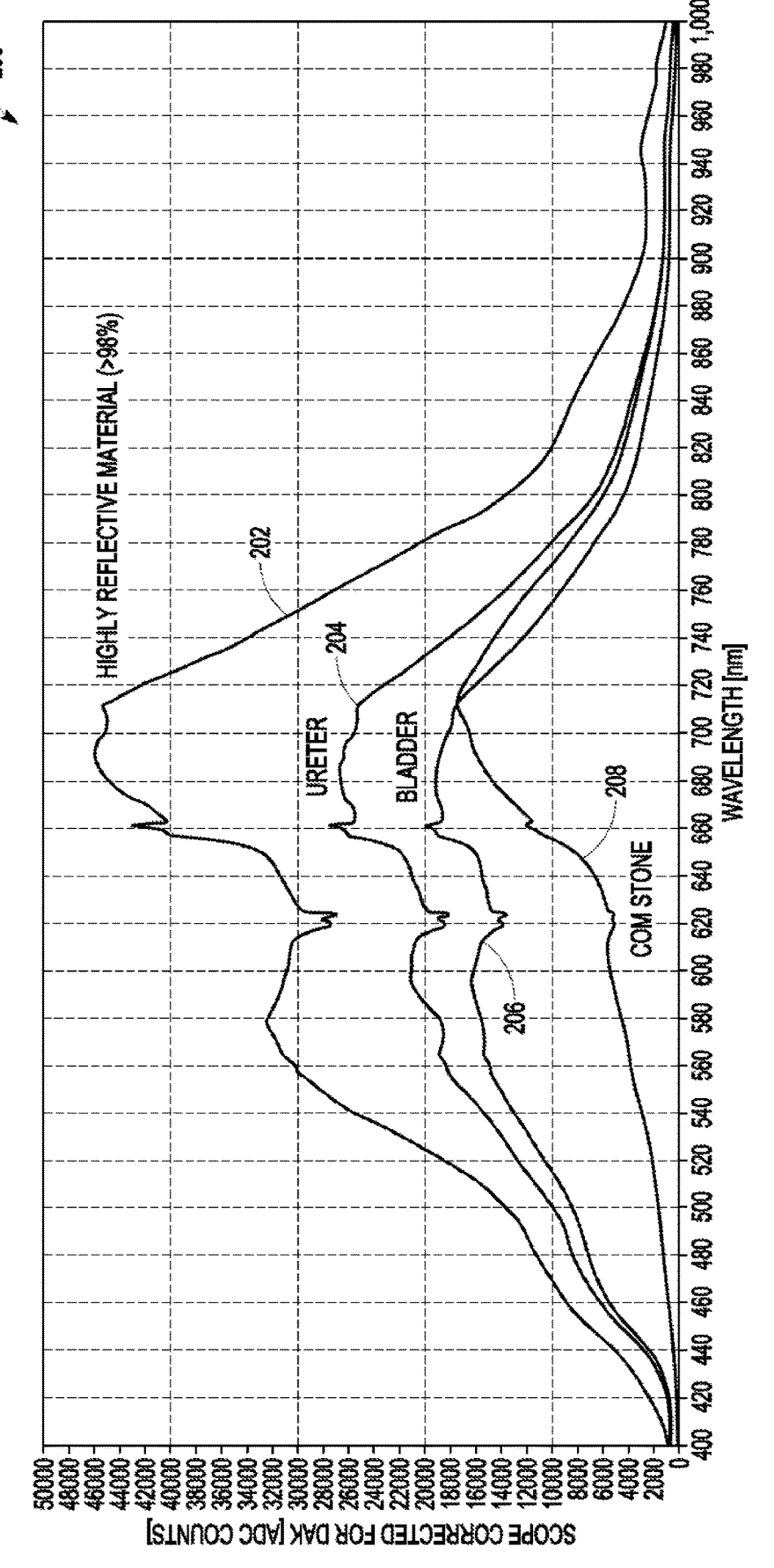
FIG. 2 illustrates an example of a graph of reflection spectra of reflected signals from different material types.

FIG. 2 illustrates an example of a graph 200 of reflection spectra of reflected signals from different material types. As illustrated in the graph 200, when light in the visible wavelengths (e.g., 400 nm to 750 nm) is reflected from a highly reflective material, such as an object formed from MgO, there will be a much higher intensity reflection spectra. In FIG. 2, this is as shown by the highly reflective material reflection spectra 202, as opposed to the Ureter tissue reflection spectra 204, the Bladder tissue reflection spectra 206, and the calcium oxalate monohydrate (COM) stone reflection spectra 208. In an example, the upper and lower threshold values can be determined by the type of procedure and can be based on known reflection spectra signatures (e.g., intensity values). For example, when the procedure is a bladder-type procedure that is performed in the bladder, the upper threshold value can be set with respect to the peak of the bladder tissue reflection spectra 206. In that case, the upper threshold value can be set such that any value of a reflected intensity above the peak value of the bladder tissue reflection spectra 206 can trigger a warning or notification to the user, or can cause adjustment or disabling of the laser emitter. In the graph 200, the ureter tissue reflection spectra 204 has a higher peak intensity than the bladder tissue reflection spectra 206. Therefore, the upper threshold value for a procedure involving the ureter can be adjusted to be higher than the upper threshold value for a procedure involving only the bladder.

Thus, similar to the differences between stone and tissue feedback identified using the optical sensor, the "signature" or reflective frequency feedback of a shiny or highly reflective object can also be observed and analyzed by a processing unit or processing circuitry. When the system identifies such a spectra reflection signature (e.g., the highly reflective material depicted in FIG. 2), the energy output from a laser can be automatically stopped or reduced by the system, or as discussed above, a warning (e.g., audible, visual, and/or sensory) alerting a user can be issued, or any combination thereof can be performed or undertaken. In some examples, adjustment of the laser can be overridden at the discretion of the physician. But any warning and/or adjustment can provide an additional layer of safety and significantly reduce the effect on a non-target that could be caused by stray, reflected energy leakage.

FIG. 3 illustrates an example of a diagram of a method 300 for analyzing a reflected signal during an in-vivo-insertable medical procedure. The method 300 can include or comprise a number of Operations or Steps (302-310). These Operations are exemplary, and the executed method can omit one or more of the listed Operations, can repeat Operations, can include other Operations, or can execute the Operations concurrently, substantially simultaneously, or in another order, as appropriate or desired.

At 302, a first signal having a first spectrum, (e.g., a non-visible spectrum) or wavelength can be emitted from a first light source (e.g., laser source) included within a surgical scope such as an endoscope. For example, the first light source emitter can be configured to emit light in a wavelength in a range between 800 nm and 900 nm (or any suitable or desired wavelength or range of wavelengths). The first signal can be emitted through a laser and/or surgical fiber coupled to the medical scope, such as toward a target that can be an object such as a kidney stone or a gallstone, a tumor, a piece of tissue or any similar target located within the body of a patient during an in-vivo-insertable medical procedure. The target can also correspond to a medical device such as a guidewire, a clamp, etc., or can correspond to an implanted device such as a stent, a screw, or the like. The first light source can include a laser that can emit laser light (e.g., a green light or a blue light laser). The laser light can be emitted from a laser diode, which can be used as a therapeutic laser (e.g., an ablation laser) during the medical procedure.

At 304, a second signal, having a second spectrum (e.g., a visible spectrum) or wavelength, can be emitted from a second light source emitter that can be included within, attached to, or coupled to the surgical scope. In an example, the second light source emitter can be configured to emit light with a wavelength in a range between 400 nm and 750 nm, or any suitable visible wavelength. The second light source emitter can be connected to a surgical fiber and/or laser fiber such that the second signal can be emitted through the laser and/or surgical fiber (such as through an aiming beam channel of the laser fiber). Alternatively, the second light source emitter can be a light source of the surgical scope (such as an endoscopic light source) coupled or attached to the physical scope. Thus, the first signal (the laser signal) and the second signal (the visible light signal) can be emitted independently of each other (e.g., the visible light signal can be emitted before the laser signal is emitted), at the same time as each other, or in an alternating manner. For example, the visible light signal can be emitted while the laser light signal is being pulsed, such as when the laser is pulsed "off". Thus, the laser signal and the visible light signal can be emitted at any time desired or appropriate during the medical procedure, and any sequence of emissions of the laser light and the visible light can be different during different medical procedures.

In another example, the laser signal and/or the visible light signal can be emitted as a "check pulse." For example, such a check pulse can include a low-power output of the laser signal or a combination of the laser signal and the visible light signal. The check-pulse can be issued and used to help ensure that a further full-power output is not likely to be reflected. This can help further limit the potential damage from reflected energy. The check pulse can last for less than a second, such as tens of microseconds, hundreds of milliseconds, nanoseconds, or any desired or appropriate length of time. Additionally, or alternatively, an additional infrared (IR) light source having an emission intensity or wavelength close to that of the laser emitter can be used to check reflection of the target. The IR light emission can be performed before any laser output, without risk of stray laser emission affecting non-target tissue.

At 306, a third signal can be returned from a surface of an object. The third signal from the object can include a reflected signal, a scattered signal (e.g., via RAMAN scattering), a fluorescence signal, or the like. For example, at least a portion of the first signal emitted at 302 and/or the second signal emitted at 304 can be reflected back from the object. The object can include a target such as a stone, tissue from a portion of a patient's anatomy, a medical device being used in the medical procedure (e.g., a guide wire), an implanted device, such as a stent, or any object or target that can be encountered during the procedure.

At 308, at least one of a spectral signature or a reflected intensity of the third signal can be compared to a criterion. In an example, the returned third signal can be analyzed to determine a reflected relative or absolute intensity of the third signal. Additionally, or alternatively, an absolute or relative spectral intensity or spectral signature across various spectral wavelengths of the third signal can be analyzed to determine one or more characteristics of the object such as the material composition of the object. At 310, responsive to meeting the at least one criterion, such as at least the spectral signature indicating that emission from the first light source emitter to the object would result in undesired damage or effect, or the reflected intensity of the third signal falling below a lower-threshold value or exceeding an upper-threshold value, a warning can be communicated, such as through a user interface, to a physician or other user, and/or an adjustment can be made to the laser signal. For example, the warning to the physician can include an audio warning such as an audible alarm or signal, the warning can include a visual warning such as by blinking the aiming beam or other visible light, changing the color of the illumination, aiming, or other visible light, communicating a text warning to a graphical user interface such as a monitor, display, or the like. Additionally, or alternatively, the warning can be haptic, such as by causing a handpiece of the medical scope to vibrate, or can be a combination of an audible, visual, or haptic warning.

In addition to, or in conjunction with the warning, the laser signal can be adjusted, such as can be based on the reflected intensity of the third signal. For example, when the reflected intensity of the third signal exceeds the upper-threshold value, which, as discussed above, can correspond to the visible light signal being reflected off of a highly-reflective object, the intensity of the laser signal can be changed (lowered or reduced) or the laser emitter can be disabled entirely. This can optionally be carried out automatically, such as without requiring user input or confirmation. In an example, the adjustment can include providing a recommendation to be communicated to the user to suggest that the user reduce the laser intensity. For example, such a recommendation can include one or more recommended settings for the laser emitter to be changed to, which the user can accept or reject, as desired, and any such settings can then be changed in accordance with such user input. In such an example, the recommended settings can be included as a part of a visual warning, or in combination with the audible warning, such as through a displayed notification box that pops up on a user interface along with a chime, beep, or other sound. In another example, the system can implement the change automatically such as by using controller circuitry or other componentry of a computer or machine such as described below with respect to FIG. 4. In some surgical procedures, such as in the removal of a previously implanted surgical mesh, a reflected signal with a high reflected intensity can indicate the presence of an object to be cut by the laser. In such a case, the laser emitter can be activated or enabled such as to cause an appropriate amount or intensity of laser light or radiation to be emitted at the target for performing such laser-cutting. Thus, the intensity value of the reflected signal can be used to determine whether to enable or disable the laser emission and/or at what intensity the laser radiation should be emitted, whether implemented automatically without requiring user intervention, by controller circuitry, or implemented as a recommendation for a user to accept or reject.

Figure 4:
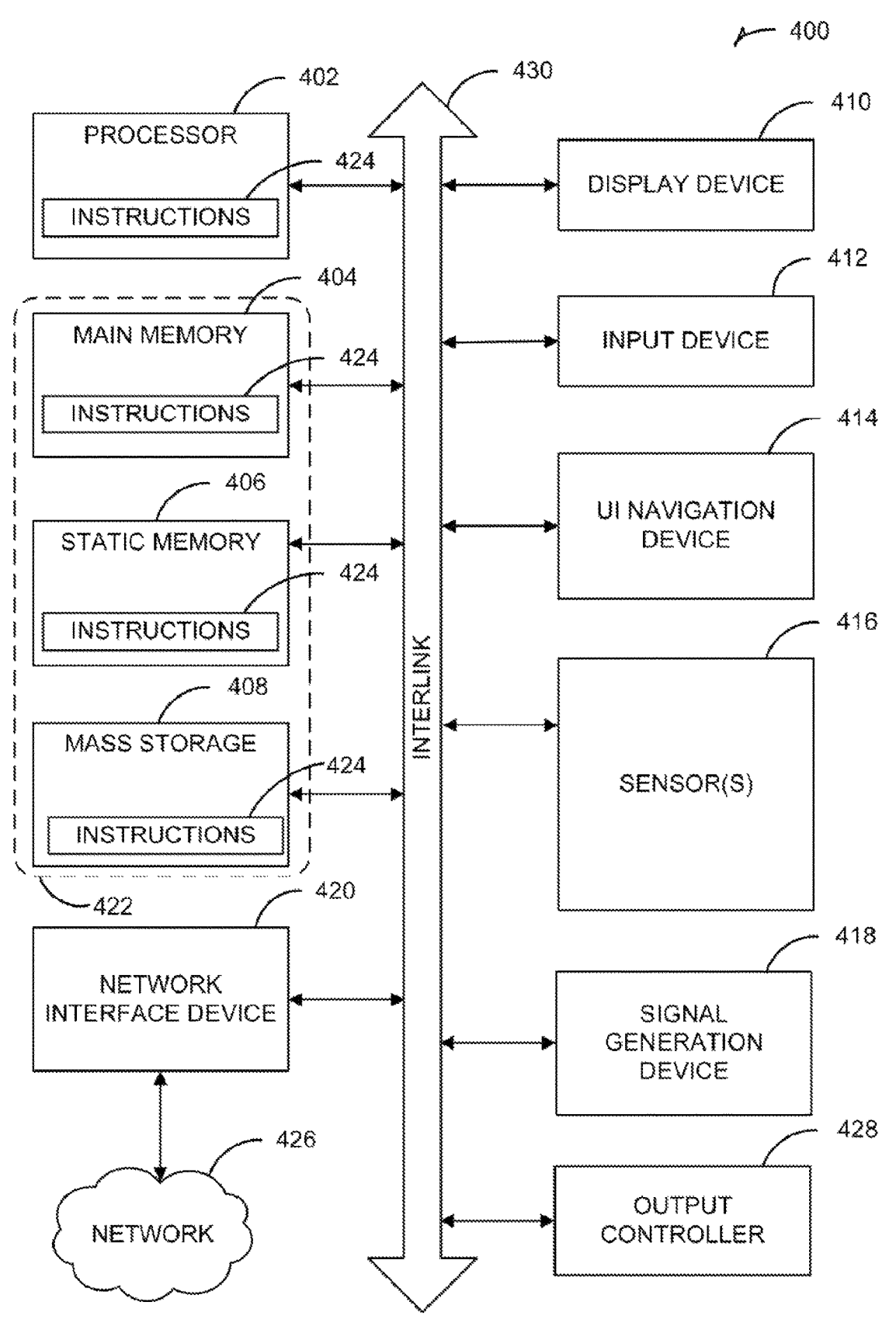
FIG. 4 is a block diagram illustrating an example of a machine upon which one or more embodiments may be implemented.

FIG. 4 is a block diagram of an example of a machine 400 upon which any one or more of the techniques (e.g., methodologies) discussed herein can perform. The machine 400 can operate as a standalone device or can be connected (e.g., networked) to other machines. For example, the machine 400 can be coupled to or connected to the optical sensor and/or the controller circuitry to cause the controller circuitry and/or the optical sensor to perform one or more of their operations described above. In another example, the machine 400 can include the controller circuitry or the optical sensor as a part of its architecture. In a networked deployment, the machine 400 can operate in the capacity of a server machine, a client machine, or both in server-client network environments. In an example, the machine 400 can act as a peer machine in peer-to-peer (P2P) (or other distributed) network environment. The machine 400 can be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, can include, or can operate by, logic or a number of components, or mechanisms. Circuit sets are a collection of circuits implemented in tangible entities that include hardware (e.g., simple circuits, gates, logic, etc.). Circuit set membership can be flexible over time and underlying hardware variability. Circuit sets include members that can, alone or in combination, perform specified operations when operating. In an example, hardware of the circuit set can be immutably designed to carry out a specific operation (e.g., hardwired). In an example, the hardware of the circuit set can include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components can be used in more than one member of more than one circuit set. For example, under operation, execution units can be used in a first circuit of a first circuit set at one point in time and reused by a second circuit in the first circuit set, or by a third circuit in a second circuit set at a different time.

Machine 400 (e.g., computer system) can include a hardware processor 402 (e.g., a central processing unit (CPU), a graphics processing unit (GPU), a hardware processor core, field programmable gate array (FPGA), or any combination thereof), a main memory 404 and a static memory 406, some or all of which can communicate with each other via an interlink (e.g., bus) 430. The machine 400 can further include a display unit 410, an alphanumeric input device 412 (e.g., a keyboard), and a user interface (UI) navigation device 414 (e.g., a mouse). In an example, the display unit 410, input device 412 and UI navigation device 414 can be a touch screen display. The machine 400 can additionally include a storage device 408 (e.g., drive unit), a signal generation device 418 (e.g., a speaker), a network interface device 420, and one or more sensors 416, such as a global positioning system (GPS) sensor, compass, accelerometer, or other sensor. The machine 400 can include an output controller 428, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 408 can include a machine readable medium 422 on which is stored one or more sets of data structures or instructions 424 (e.g., software) embodying or used by any one or more of the techniques or functions described herein. The instructions 424 can also reside, completely or at least partially, within the main memory 404, within static memory 406, or within the hardware processor 402 during execution thereof by the machine 400. In an example, one or any combination of the hardware processor 402, the main memory 404, the static memory 406, or the storage device 408 can constitute machine readable media.

While the machine readable medium 422 is illustrated as a single medium, the term "machine readable medium" can include a single medium or multiple media (e.g., a centralized or distributed database, and/or associated caches and servers) configured to store the one or more instructions 424.

The term "machine readable medium" can include any medium that is capable of storing, encoding, or carrying instructions for execution by the machine 400 and that cause the machine 400 to perform any one or more of the techniques of the present disclosure, or that is capable of storing, encoding, or carrying data structures used by or associated with such instructions. Non-limiting machine readable medium examples can include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media can include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 424 can further be transmitted or received over a communications network 426 using a transmission medium via the network interface device 420 utilizing any one of a number of transfer protocols (e.g., frame relay, internet protocol (IP), transmission control protocol (TCP), user datagram protocol (UDP), hypertext transfer protocol (HTTP), etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards), IEEE 802.15.4 family of standards, peer-to-peer (P2P) networks, among others. In an example, the network interface device 420 can include one or more physical jacks (e.g., Ethernet, coaxial, or phone jacks) or one or more antennas to connect to the communications network 426. In an example, the network interface device 420 can include a plurality of antennas to wirelessly communicate using at least one of single-input multiple-output (SIMO), multiple-input multiple-output (MIMO), or multiple-input single-output (MISO) techniques. The term "transmission medium" shall be taken to include any tangible medium that is capable of storing, encoding, or carrying instructions for execution by the machine 400, and includes digital or analog communications signals or other tangible medium to facilitate communication of such software.

Figure 5:
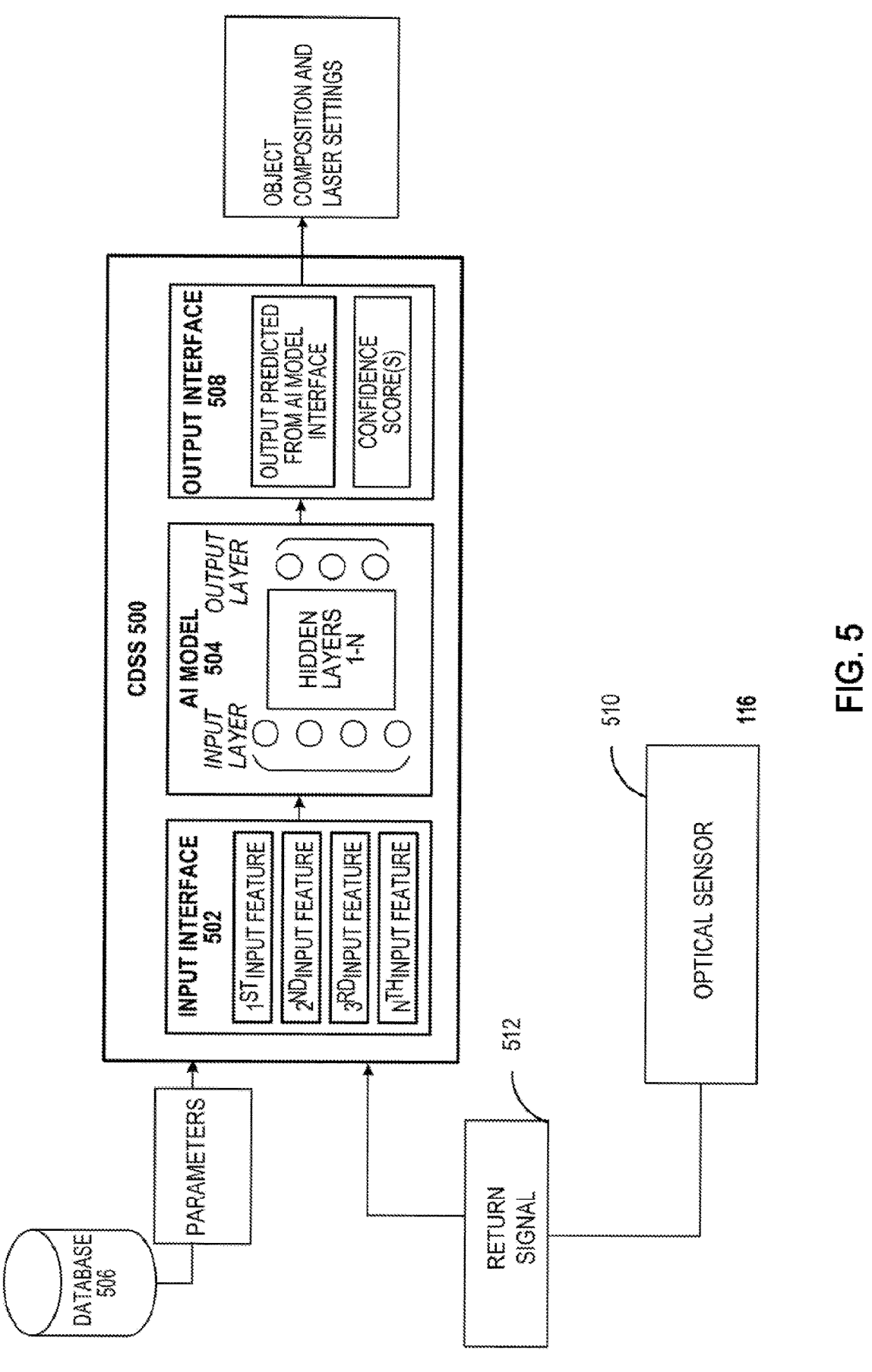
FIG. 5 illustrates an example of a schematic diagram of an exemplary computer-based clinical decision support system (CDSS).

FIG. 5 illustrates a schematic diagram of an exemplary computer-based clinical decision support system (CDSS) 500 that can be configured to determine information or characteristics about an object based on a reflected intensity of a signal returned from the object. The information or characteristics of the object can include a material composition (such as whether the object is made from a material such as stainless steel, magnesium oxide, a polymer, etc.), and based on the composition can determine recommended, optimal, or ideal settings of the laser being used during the laser procedure (such as an ideal laser intensity, whether the laser emitter should be disabled), or the like. The CDSS 500 can also adjust one or more settings or recommend an adjustment of one or more settings of the laser to the physician. The CDSS 500 can include an input interface 502 through which parameters such as the size of a surgical fiber, information about the light sources, information about the optical components, and/or information about the scope which are specific to a patient's procedure can be provided as input features to an artificial intelligence (AI) model 504, a processor which performs an inference operation in which the parameters are applied to the AI model to generate the determination of the object's composition and one or more adjusted laser settings, and an output interface 508 through which the determined composition and adjusted setting(s) can be communicated to a user, e.g., a clinician.

The input interface 502 can include a direct data link between the CDSS 500 and one or more medical devices that generate at least some of the input features. For example, the input interface 502 can transmit information about the light sources and/or the optical components (e.g., frequency or wavelength of signals from the light sources or aiming beam emission sources, or information about a signal returned from the object directly to the CDSS 500 during a therapeutic and/or diagnostic medical procedure. In an example, information about the light sources and/or the optical components, the scope, etc., used during the procedure can be stored in a database 506. Additionally, or alternatively, the input interface 502 can be a classical user interface that facilitates interaction between a user and the CDSS 500. For example, the input interface 504 can facilitate a user interface through which the user can manually enter the information about the surgical fiber, the scope, the optical components, signals to block or allow, reflective intensity threshold values, etc. Additionally, or alternatively, the input interface 502 can provide the CDSS 500 with access to an electronic patient record or the components being used during the procedure from which one or more input features can be extracted. In any of these cases, the input interface 502 can be configured to collect one or more of the following input features in association with one or more of a specific patient, a type of medical procedure, a type of scope, reflected intensity threshold values, or the like, on or before a time at which the CDSS 500 is used to assess the input features will take place.

An example of an input feature can include a type of the surgical fiber to be used during the procedure.

An example of an input feature can include a type of light or laser source.

An example of an input feature can include the type of scope being used during the procedure.

An example of an input feature can include a wavelength or frequency of the light and/or laser source.

An example of an input feature can include a reflective intensity upper-threshold value.

An example of an input feature can include a reflected intensity lower-threshold value.

An example of an input feature can include signal information of a return signal 512 received at the optical sensor 510 from the target or object.

Based on one or more of the above input features, the processor can perform an inference operation using the AI model 504 to generate a determined composition of the object from which the signal is returned based on the reflected intensity, and determined ideal or optimal laser settings, and any adjustments needed to the current settings of the laser. For example, input interface 502 can deliver the one or more of the input features listed above into an input layer of the AI model 504 which propagates these input features through the AI model 504 to an output layer. The AI model 504 can provide a computer system the ability to perform tasks, without explicitly being programmed, by making inferences based on patterns found in the analysis of data. The AI model 504 explores the study and construction of algorithms (e.g., machine-learning algorithms) that can learn from existing data and make predictions about new data. Such algorithms operate by building an AI model from example training data in order to make data-driven predictions or decisions expressed as outputs or assessments.

Examples of two modes for machine learning (ML) can include: supervised ML and unsupervised ML. Supervised ML uses prior knowledge (e.g., examples that correlate inputs to outputs or outcomes) to learn the relationships between the inputs and the outputs. The goal of supervised ML is to learn a function that, given some training data, best approximates the relationship between the training inputs and outputs so that the ML model can implement the same relationships when given inputs to generate the corresponding outputs. Unsupervised ML is the training of an ML algorithm using information that is neither classified nor labeled and allowing the algorithm to act on that information without guidance. Unsupervised ML is useful in exploratory analysis because it can automatically identify structure in data.

Tasks for supervised ML can include classification problems and regression problems. Classification problems, also referred to as categorization problems, aim at classifying items into one of several category values (for example, is this object an apple or an orange?). Regression algorithms aim at quantifying some items (for example, by providing a score to the value of some input). Some examples of supervised-ML algorithms are Logistic Regression (LR), Naive-Bayes, Random Forest (RF), neural networks (NN), deep neural networks (DNN), matrix factorization, and Support Vector Machines (SVM).

Some possible tasks for unsupervised ML include clustering, representation learning, and density estimation. Some examples of unsupervised-ML algorithms are K-means clustering, principal component analysis, and autoencoders.

Another type of ML is federated learning (also known as collaborative learning) that trains an algorithm across multiple decentralized devices holding local data, without exchanging the data. This approach stands in contrast to traditional centralized machine-learning techniques where all the local datasets are uploaded to one server, as well as to more classical decentralized approaches which often assume that local data samples are identically distributed. Federated learning enables multiple actors to build a common, robust machine learning model without sharing data, thus allowing to address critical issues such as data privacy, data security, data access rights and access to heterogeneous data.

In some examples, the AI model 504 can be trained continuously or periodically prior to performance of the inference operation by the processor. Then, during the inference operation, the patient specific input features provided to the AI model 504 can be propagated from an input layer, through one or more hidden layers, and ultimately to an output layer that corresponds to the information about the object. For example, when evaluating the reflected intensity of the signal from the target, the system can determine one or more characteristics of the object and determine laser settings that should be used and/or adjusted based on the one or more characteristics.

During and/or subsequent to the inference operation, the information about the object can be communicated to the user via the output interface 508 (e.g., a user interface (UI)) and/or automatically cause a surgical laser connected to the processor to perform a desired action. Therefore, based on the composition of the object, for example, if the system determines the object is a kidney stone, the system can cause the surgical laser to emit energy to ablate the stone, adjust the amount of ablation energy, move a portion of the scope, etc. Conversely, if the system determines the object to be a guide wire or a medical instrument that represents a non-target (e.g., not a part of the medical procedure) or non-target tissue, the system can disable the laser emitter, cause the surgical fiber to be repositioned, or take any other appropriate steps to limit or reduce the chance of stray radiation energy contacting the object.

ADDITIONAL NOTES & EXAMPLES

Example 1 is a system for determining a characteristic of an object during a laser procedure, the system comprising: a surgical scope; a first light source emitter, coupled to or included within the surgical scope, configurable to emit a first signal having a first spectrum; a second light source emitter, coupled to or included within the surgical scope, configurable to emit a second signal having a second spectrum, different from the first spectrum; an optical sensor, configurable to detect a third signal from a surface of the object in response to the emitted second signal; and controller circuitry, coupled to the optical sensor, configured to (i) compare at least one of a spectral signature of the third signal or a reflected intensity of the third signal to at least one criterion and, when the at least one criterion is met, (ii) to cause at least one of sending a warning to a user or adjusting a setting of the first light source emitter.

In Example 2, the subject matter of Example 1 optionally includes wherein the at least one criterion includes an indication in the spectral signature that emission from the first light source emitter to the object would result in undesired damage.

In Example 3, the subject matter of any one or more of Examples 1-2 optionally include wherein the at least one criterion includes a determination that the reflected intensity of the third signal falls below a lower-threshold value or exceeds an upper-threshold value.

In Example 4, the subject matter of Example 3 optionally includes wherein the reflected intensity of the third signal exceeding the upper-threshold value corresponds to the object being comprised of one or more of: magnesium oxide (MgO), stainless steel, nitinol, a fluoropolymer, a polymer, or a plastic.

In Example 5, the subject matter of any one or more of Examples 1~4 optionally include wherein the warning includes a visual warning, and wherein the visual warning includes at least one of causing the second light source emitter to flash the second signal or to change a color of the second signal.

In Example 6, the subject matter of any one or more of Examples 1-5 optionally include wherein the surgical scope is an endoscope and wherein the second light source emitter is a visible light source connected to or included on the endoscope.

In Example 7, the subject matter of Example 6 optionally includes nm.

In Example 8, the subject matter of any one or more of Examples 1-7 optionally include wherein the first light source emitter includes at least one of a laser light source or an aiming beam light source emitted through a surgical fiber connected to the surgical scope.

In Example 9, the subject matter of Example 8 optionally includes wherein the first light source emitter includes at least one of a blue light laser or a green light laser.

In Example 10, the subject matter of any one or more of Examples 8-9 optionally include wherein the second light source emitter includes at least one of a visible light source or an infrared (IR) light source connected to the surgical fiber such that the second signal is emitted through the surgical fiber.

In Example 11, the subject matter of any one or more of Examples 8-10 optionally include nm.

In Example 12, the subject matter of any one or more of Examples 1-11 optionally include wherein to adjust the first signal includes at least one of changing an intensity of the first signal or disabling the first light source emitter.

In Example 13, the subject matter of any one or more of Examples 1-12 optionally include a spectrometer configured to perform spectroscopic analysis of the third signal, and wherein, responsive to the reflected intensity of the third signal meeting the at least one criterion, the controller circuitry causes the spectrometer to interrupt or terminate spectral analysis of the third signal.

Example 14 is a method for determining a characteristic of an object during a laser procedure, the method comprising: emitting a first signal having a first spectrum from a first light source emitter coupled to or included within a surgical scope; emitting a second signal having a second spectrum, different from the first spectrum, from a second light source emitter coupled to or included within the surgical scope; receiving a third signal from a surface of the object in response to the emitted second signal at an optical sensor connected to the surgical scope; comparing, using the optical sensor, at least one of a spectral signature or a reflected intensity of the received third signal to at least one criterion; and when the at least one criterion is met, sending at least one of a warning to a user or adjusting a setting of the first light source emitter.

In Example 15, the subject matter of Example 14 optionally includes wherein adjusting the first signal includes at least one of changing an intensity of the first signal or disabling the first light source emitter.

In Example 16, the subject matter of any one or more of Examples 14-15 optionally include wherein the at least one criterion includes an indication in the spectral signature that emission from the first light source emitter to the object would result in undesired damage.

In Example 17, the subject matter of any one or more of Examples 14-16 optionally include wherein emitting at least one of the first signal or the second signal includes pulsing at least one of the first light source emitter or the second light source emitter for a period of time.

Example 18 is a system for to determine a characteristic of an object during a laser procedure, the system comprising: a processor; a user interface (UI); and memory, including instructions that, when executed by the processor, cause the processor to execute operations to: emit a first signal having a first spectrum from a first light source emitter coupled to or included within a surgical scope; emit a second signal having a second spectrum, different from the first spectrum, from a second light source emitter coupled to or included within the surgical scope; receive a third signal from a surface of the object in response to the emitted second signal at an optical sensor connected to the surgical scope; compare, using the optical sensor, at least one of a spectral signature or a reflected intensity of the third signal to at least one criterion, wherein the at least one criterion includes an indication in the spectral signature that emission from the first light source emitter would result in undesired damage; and when the at least one criterion is met, cause a warning to be sent to the UI or adjusting a setting of the first light source emitter.

In Example 19, the subject matter of Example 18 optionally includes wherein the first light source emitter includes a laser light source or an aiming beam light source emitted through a surgical fiber connected to the surgical scope, and wherein the second light source emitter includes at least one of a visible light source or an infrared (IR) light source connected to the surgical fiber such that the second signal is emitted through the surgical fiber.

In Example 20, the subject matter of any one or more of Examples 18-19 optionally include wherein the first light source emitter includes at least one of a blue light laser or a green light laser.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is to allow the reader to quickly ascertain the nature of the technical disclosure and is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the embodiments should be determined with reference to the appended claims, along with the full scope of equivalents to which such claims are entitled.

What is claimed is:

1. A system for determining a characteristic of an object during a laser procedure, the system comprising:
   a surgical scope;
   a first light source emitter, coupled to or included within the surgical scope, configurable to emit a first signal having a first spectrum;
   a second light source emitter, coupled to or included within the surgical scope, configurable to emit a second signal having a second spectrum, different from the first spectrum;
   an optical sensor, configurable to detect a third signal from a surface of the object in response to the emitted second signal;
   controller circuitry, coupled to the optical sensor, configured to (i) compare at least one of a spectral signature of the third signal or a reflected intensity of the third signal to at least one criterion and, when the at least one criterion is met, (ii) to cause at least one of sending a warning to a user or adjusting a setting of the first light source emitter; and
   a spectrometer configured to perform spectroscopic analysis of the third signal, wherein, responsive to the reflected intensity of the third signal meeting the at least one criterion, the controller circuitry causes the spectrometer to interrupt or terminate spectral analysis of the third signal.

2. The system of claim 1, wherein the at least one criterion includes an indication in the spectral signature that emission from the first light source emitter to the object would result in undesired damage.

3. The system of claim 1, wherein the at least one criterion includes a determination that the reflected intensity of the third signal falls below a lower-threshold value or exceeds an upper-threshold value.

4. The system of claim 3, wherein the reflected intensity of the third signal exceeding the upper-threshold value corresponds to the object being comprised of one or more of: magnesium oxide (MgO), stainless steel, nitinol, a fluoropolymer, a polymer, or a plastic.

5. The system of claim 1, wherein the warning includes a visual warning, and wherein the visual warning includes at least one of causing the second light source emitter to flash the second signal or to change a color of the second signal.

6. The system of claim 1 wherein the surgical scope is an endoscope and wherein the second light source emitter is a visible light source connected to or included on the endoscope.

7. The system of claim 6, wherein the second light source emitter is configured to emit light with a wavelength in a range between 400 nm and 750 nm.

8. The system of claim 1, wherein the first light source emitter includes at least one of a laser light source or an aiming beam light source emitted through a surgical fiber connected to the surgical scope.

9. The system of claim 8, wherein the first light source emitter includes at least one of a blue light laser or a green light laser.

10. The system of claim 8, wherein the second light source emitter includes at least one of a visible light source or an infrared (IR) light source connected to the surgical fiber such that the second signal is emitted through the surgical fiber.

11. The system of claim 8, wherein the first light source emitter is configured to emit light in a wavelength in a range between 800 nm and 900 nm.

12. The system of claim 1, wherein to adjust the first signal includes at least one of changing an intensity of the first signal or disabling the first light source emitter.

13. A method for determining a characteristic of an object during a laser procedure, the method comprising:
   emitting a first signal having a first spectrum from a first light source emitter coupled to or included within a surgical scope;
   emitting a second signal having a second spectrum, different from the first spectrum, from a second light source emitter coupled to or included within the surgical scope;
   receiving a third signal from a surface of the object in response to the emitted second signal at an optical sensor connected to the surgical scope;
   performing spectroscopic analysis of the third signal using a spectrometer coupled to the optical sensor;

comparing, using the optical sensor, at least one of a spectral signature or a reflected intensity of the received third signal to at least one criterion; and when the at least one criterion is met, interrupting or terminating the spectroscopic analysis and at least one of: i) sending a warning to a user or ii) adjusting a setting of the first light source emitter.

14. The method of claim 13, wherein adjusting the first signal includes at least one of changing an intensity of the first signal or disabling the first light source emitter.

15. The method of claim 13, wherein the at least one criterion includes an indication in the spectral signature that emission from the first light source emitter to the object would result in undesired damage.

16. The method of claim 13, wherein emitting at least one of the first signal or the second signal includes pulsing at least one of the first light source emitter or the second light source emitter for a period of time.

17. A system to determine a characteristic of an object during a laser procedure, the system comprising:

a processor;

a user interface (UI); and memory, including instructions that, when executed by the processor, cause the processor to execute operations to:

cause a first signal having a first spectrum to be emitted from a first light source emitter coupled to or included within a surgical scope;

cause a second signal having a second spectrum, different from the first spectrum, to be emitted from a second light source emitter coupled to or included within the surgical scope;

receive a third signal from a surface of the object in response to the emitted second signal at an optical sensor connected to the surgical scope;

cause a spectroscopic analysis of the third signal to be performed using a spectrometer coupled to the optical sensor;

cause the optical sensor to compare at least one of a spectral signature or a reflected intensity of the third signal to at least one criterion, wherein the at least one criterion includes an indication in the spectral signature that emission from the first light source emitter would result in undesired damage; and when the at least one criterion is met, cause the spectroscopic analysis to be interrupted or terminated and cause at least one of: i) a warning to be sent to the UI or ii) a setting of the first light source emitter to be adjusted.

18. The system of claim 17, wherein the first light source emitter includes a laser light source or an aiming beam light source emitted through a surgical fiber connected to the surgical scope, and wherein the second light source emitter includes at least one of a visible light source or an infrared (IR) light source connected to the surgical fiber such that the second signal is emitted through the surgical fiber.

19. The system of claim 17, wherein the first light source emitter includes at least one of a blue light laser or a green light laser.

*  *  *  *  *